US012778599B2

(12) United States Patent
Venturini et al.

(10) Patent No.: US 12,778,599 B2
(45) Date of Patent: Nov. 3, 2026

(54) TELESCOPIC INTRAMEDULLARY NAIL

(71) Applicant: ORTHOFIX S.R.L., Bussolengo (IT)

(72) Inventors: Daniele Venturini, Povegliano (IT); Marco Magni, Ferrara (IT)

(73) Assignee: Orthofix, S.R.L., Verona (IT)

( * ) Notice: Subject to any disclaimer, the term of this patent is extended or adjusted under 35 U.S.C. 154(b) by 0 days.

(21) Appl. No.: 18/962,910

(22) Filed: Nov. 27, 2024

(65) Prior Publication Data

US 2025/0176975 A1 Jun. 5, 2025

(30) Foreign Application Priority Data

Nov. 30, 2023 (IT) ........................ 102023000025605

(51) Int. Cl.
*A61B 17/72* (2006.01)
*A61B 17/16* (2006.01)

(52) U.S. Cl.
CPC ........ *A61B 17/164* (2013.01); *A61B 17/1662* (2013.01); *A61B 17/7241* (2013.01)

(58) Field of Classification Search
CPC . A61B 17/72; A61B 17/7216; A61B 17/7283; A61B 17/7225
See application file for complete search history.

(56) References Cited

U.S. PATENT DOCUMENTS 4,858,602 A * 8/1989 Seidel ................ A61B 17/7241 606/62
6,443,954 B1 * 9/2002 Bramlet ............... A61B 17/744 606/328
6,524,313 B1 2/2003 Fassier
9,060,809 B2 * 6/2015 Tipirneni ........... A61B 17/8863
9,517,094 B1 * 12/2016 Savage ................ A61B 17/744
10,433,886 B2 10/2019 Polat
10,813,673 B2 * 10/2020 Hustedt .............. A61B 17/7291
11,446,072 B2 * 9/2022 Abedian ............ A61B 17/1717
2004/0127898 A1 * 7/2004 Adam .................... A61B 17/72 606/64
2005/0216007 A1 * 9/2005 Woll .................. A61B 17/7258 606/62
2007/0233101 A1 * 10/2007 Metzinger .............. A61B 17/72 606/62

(Continued)

FOREIGN PATENT DOCUMENTS

IT 102019000003285 B1 * 2/2021
JP 6271418 B2 1/2018

(Continued)

OTHER PUBLICATIONS

Ministero Delle Imprese E Del Made in Italy, Search Report, IT 202300025605, Apr. 22, 2024, 2 pages, Munich.

*Primary Examiner* — Jacqueline T Johanas
(74) *Attorney, Agent, or Firm* — Haynes and Boone, LLP

(57) ABSTRACT

A telescopic intramedullary nail for the treatment of fractures or deformations of long bones, such as for example in the case of osteogenesis imperfecta or pseudoarthrosis, extended along a longitudinal axis. The telescopic intramedullary nail may include a hollow stem and a rod telescopically coupled inside said hollow stem. A structure may constrain the hollow stem and said rod in rotation about said longitudinal axis during the insertion and/or during the removal of said telescopic intramedullary nail.

13 Claims, 6 Drawing Sheets

(56) References Cited

U.S. PATENT DOCUMENTS

| | | | | |
|---|---|---|---|---|
| 2011/0190769 | A1* | 8/2011 | Haininger .......... | A61B 17/8061 606/64 |
| 2013/0116693 | A1* | 5/2013 | Nelson ............... | A61B 17/7266 606/64 |
| 2013/0116694 | A1 | 5/2013 | Zurschmiede | |
| 2014/0214034 | A1 | 7/2014 | Rayes | |
| 2015/0327902 | A1* | 11/2015 | Eekhoff ............. | A61B 17/8891 606/310 |
| 2018/0042651 | A1* | 2/2018 | Little ................. | A61B 17/7283 |
| 2018/0064475 | A1* | 3/2018 | Polat ...................... | A61B 17/72 |
| 2019/0038325 | A1* | 2/2019 | Lorenzini .......... | A61B 17/8894 |
| 2019/0133650 | A1* | 5/2019 | Haaja ................. | A61B 17/8004 |
| 2020/0197054 | A1* | 6/2020 | Dadourian ......... | A61B 17/7283 |
| 2022/0015810 | A1* | 1/2022 | Haaja ................. | A61B 17/8004 |
| 2022/0304730 | A1* | 9/2022 | Beckett .............. | A61B 17/7225 |
| 2023/0149059 | A1* | 5/2023 | Rzasa ................ | A61B 17/7291 606/62 |
| 2025/0176975 | A1* | 6/2025 | Venturini ............... | A61B 17/72 |
| 2025/0177016 | A1* | 6/2025 | Venturini ............... | A61B 17/72 |
| 2025/0221746 | A1* | 7/2025 | Zavani ............... | A61B 17/8685 |
| 2025/0255652 | A1* | 8/2025 | Wallace ............... | A61B 17/744 |

FOREIGN PATENT DOCUMENTS

| | | | | | |
|---|---|---|---|---|---|
| RU | 195578 | U1 * | 1/2020 | ......... | A61B 17/7216 |
| WO | WO-2020178287 | A1 * | 9/2020 | ......... | A61B 17/7233 |
| WO | WO-2021242211 | A1 * | 12/2021 | ............. | A61B 17/72 |

* cited by examiner

TELESCOPIC INTRAMEDULLARY NAIL

PRIORITY

This application claims priority to Italy Patent Application No. 102023000025605 filed on Nov. 30, 2023, incorporated herein by reference in its entirety.

FIELD OF THE INVENTION

The present invention relates to a nail which can be inserted into the long bones of a patient, preferably femur, tibia or humerus.

In particular, the invention relates to a telescopic intramedullary nail intended for the treatment of fractures or deformations of long bones, such as for example in the case of osteogenesis imperfecta or pseudoarthrosis, in particular in childhood.

The telescopic intramedullary nail according to the invention is preferably intended to be implanted with an anterograde approach.

The invention is usefully applied in the field of paediatric orthopedics, for example for interventions to correct bone deformities of long bones due to osteogenesis imperfecta or congenital pseudoarthrosis. Therefore, the following description is made for use in the context of this field but it is not to be understood as limiting.

BACKGROUND

Known techniques for correcting long bone deformations in developmental-age patients affected by osteogenesis imperfecta provide to make at least one osteotomy, the alignment of bone fragments and the insertion of a nail into the medullary cavity or other cavity obtained along the bone.

The nails used in this type of interventions are of the telescopic type, that is they provide a hollow stem and a rod which is fixable and slidingly inserted into said hollow stem, the ends of the hollow stem and of the rod being constrained to the two opposite ends of the long bone, respectively. The relative sliding of the two components during the bone growth allows the nail to adapt to the length variation of the bone itself ensuring that the alignment is maintained.

Telescopic intramedullary nails of the Fassier-Duval type, which adopt an anterograde surgical approach, are widely used in the prior art. In fact, the anterograde approach is almost mandatory in tibia applications, where an access from the ankle joint has high risks of damaging the joint itself, and in many cases it is preferred in femur applications as well to avoid entering from the knee joint.

In the above Fassier-Duval nail it is provided that the rod has a threaded tip arranged to be screwed into a distal epiphysis of the long bone, while the hollow stem inside which the rod slides has a threaded head which can be screwed into the proximal epiphysis with respect to the operation point.

The threaded tip is thus fixed beyond the growth cartilage. The rod, having the tip fixed to the distal end of the bone, moves inside the hollow stem during growing, so that the nail adapts to the progressive lengthening of the bone.

The surgical technique for implanting the Fassier-Duval nail provides, once the osteotomies have been made and the bone fragments have been straightened, the creation of a cavity inside the bone by means of a perforator, guided by a Kirchner wire, which enlarges the medullary cavity for housing the nail components.

Once the cavity has been created, the perforator is removed.

The rod is then inserted into the cavity at an end of the bone up to screw the threaded tip into the epiphysis of the opposite end. The proximal end of the rod is then cut to measure directly on site.

The hollow stem is then inserted into the cavity so as to slidingly house the rod and the threaded head screwed into the bone.

The insertion of the nail components is performed using tools coupled to the end of the component which provides a handle to support the insertion and advance of the nail into the cavity.

The perforator used in these surgical operations provides a perforation end shaped to remove bone during the rotational advance.

Although advantageous in many respects, the Fassier-Duval nails have several drawbacks which are still unsolved to date.

A first drawback relates to the difficulty in extracting the rod component at the time of removing the nail. For the removal it is first necessary to grip this component, which is externally smooth and has a relatively small diameter, inside the medullary cavity; it is thus necessary to perform a torsion in order to unscrew the thread from the epiphysis; finally a traction is to be performed in order to extract the component from the bone. These operations are in most cases extremely complex for the surgeon.

A second drawback still relates to possible seizure problems, due to the local deformation of the rod in the point in which it is cut to measure. The rod may thus hardly enter and slide inside the hollow stem.

Finally, a third drawback derives from the selection of the correct size of the hollow stem to be used after the insertion of the rod.

The technical problem underlying the present invention is to solve or at least mitigate the drawbacks mentioned with reference to the Fassier-Duval nail.

A particular object of the present invention is to devise a telescopic intramedullary nail which allows an easy extraction of both components from the bone site.

A further particular object of the present invention is to devise a telescopic intramedullary nail which allows to avoid the cut in site of the rod, avoiding the drawbacks of device seizure at the cut.

A further object is to devise a nail which facilitates the size selection of the components at the time of implantation.

SUMMARY OF THE INVENTION

The above objects are achieved by a telescopic intramedullary nail for the treatment of fractures or deformations of long bones, such as for example in the case of osteogenesis imperfecta or pseudoarthrosis, extended along a longitudinal axis, comprising:

- a hollow stem;
- a rod telescopically coupled inside said hollow stem;
- means for constraining said hollow stem and said rod in rotation about said longitudinal axis during the insertion and/or during the removal of said telescopic intramedullary nail.

The idea underlying the present invention is to insert the two nail components already assembled, so as to avoid cutting the rod. Moreover, the rotational constraint between the parts also allows to extract both components with a single rotation, facilitating the otherwise difficult recovery of the rod.

The means for constraining said hollow stem and said rod in rotation comprise at least one shaped section of said hollow stem and one counter-shaped section of said rod, said shaped section and said counter-shaped section having respective internal and external profiles which are non-circular and shaped in a complementary manner.

The counter-shaped section does not involve the whole extension of the rod, a remaining section being cylindrical.

Always preferably, the shaped section does not involve the whole extension of the hollow stem, a remaining section having a cylindrical internal surface.

By limiting the shaped sections it is possible to form a lock to the sliding of the rod in the hollow stem which facilitates the recovery of the telescopic intramedullary nail in a single operation at the time of removal.

Preferably, said shaped section and said counter-shaped section are placed at the distal end of the hollow stem and of the rod, respectively.

Preferably, said shaped section of the hollow stem is a sleeve added, in particular welded, to the distal end of a remaining section defined by an internally cylindrical tube.

Said counter-shaped section preferably comprises one or more flat faces, which can be easily made in a machine tool, in an otherwise cylindrical geometry. Preferably, these flat faces do not extend up to the proximal end of the rod.

In a particularly advantageous manner, the above means for constraining said hollow stem and said rod in rotation can comprise a front shaping at the distal end of said hollow stem arranged to engage with a front counter-shaping of the rod made on a shoulder facing the hollow stem. The front shaping and counter-shaping engage only when the hollow stem is in a distal end-of-stroke position with respect to the rod, which can occur in particular in the nail insertion step. The front shaping and counter-shaping allow therefore to transmit a greater torque in the critical step of screwing the anchor tip into the epiphysis of the patient.

Preferably the rod comprises, at the distal end thereof, an anchor tip, which is in particular threaded, configured to be internally fixed inside the distal epiphysis of the long bone of a patient.

Preferably, the hollow stem comprises a terminal head arranged to externally abut against a proximal cortical of the long bone of a patient.

Preferably, said terminal head is removably associated with a proximal end of the hollow stem.

In particular, the proximal end of the hollow stem can comprise coupling means for the selective coupling of said terminal head or of a tool for inserting and/or removing the telescopic intramedullary nail.

Said coupling means can comprise an internal thread and a possible end crenelation made frontally with respect to the internal thread.

The nail according to the invention is preferably an anterograde nail, i.e. intended to be implanted with a preferably anterograde surgical approach.

Further features and advantages of the telescopic intramedullary nail according to the present invention will be more apparent from the following description of an exemplary embodiment given by way of non-limiting example.

BRIEF DESCRIPTION OF THE DRAWINGS

The present description refers to the attached drawings, in which.

In different figures, similar elements will be indicated with similar reference numbers.

DETAILED DESCRIPTION OF THE EMBODIMENTS

Figure 1:
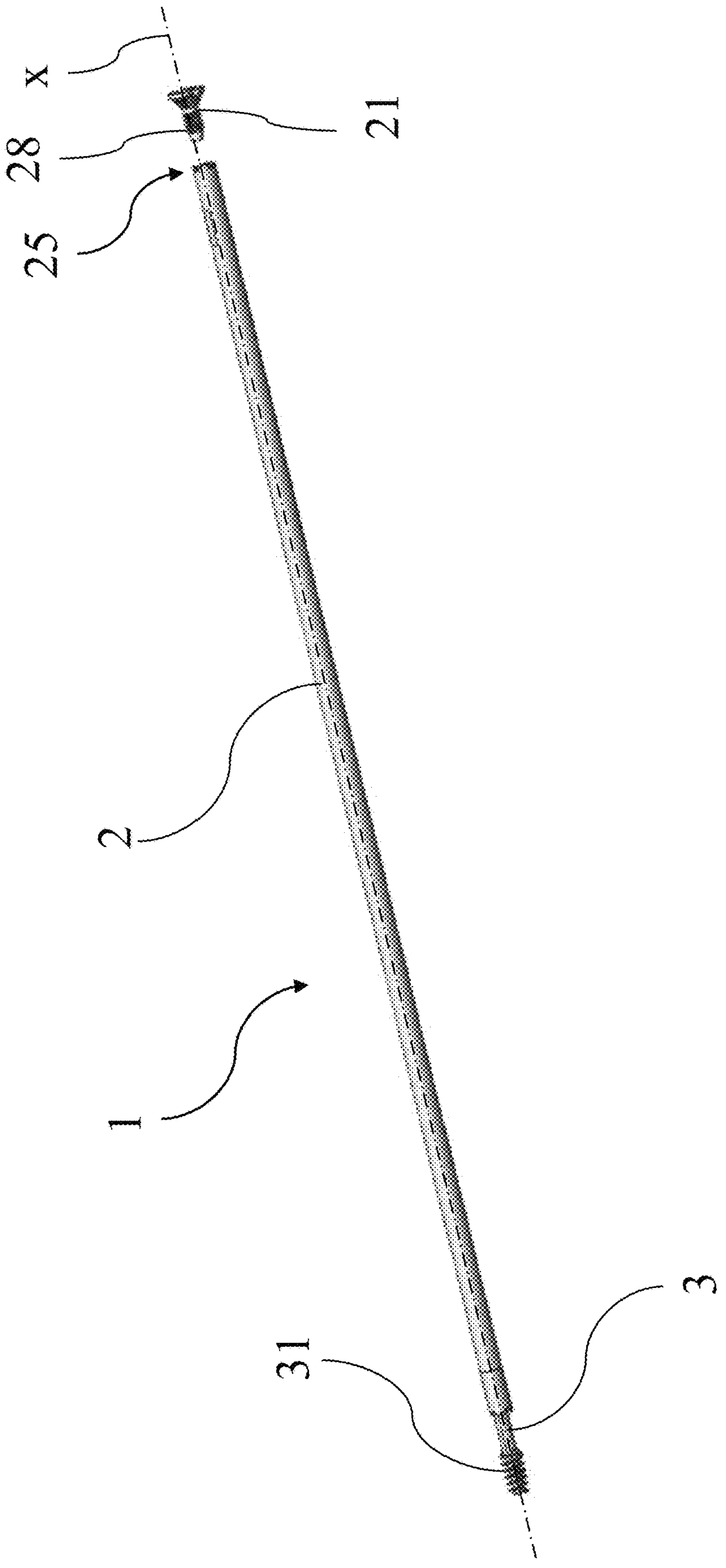
FIG. 1 shows a perspective view of an assembled telescopic intramedullary nail made in accordance with the present invention.
Figure 2:
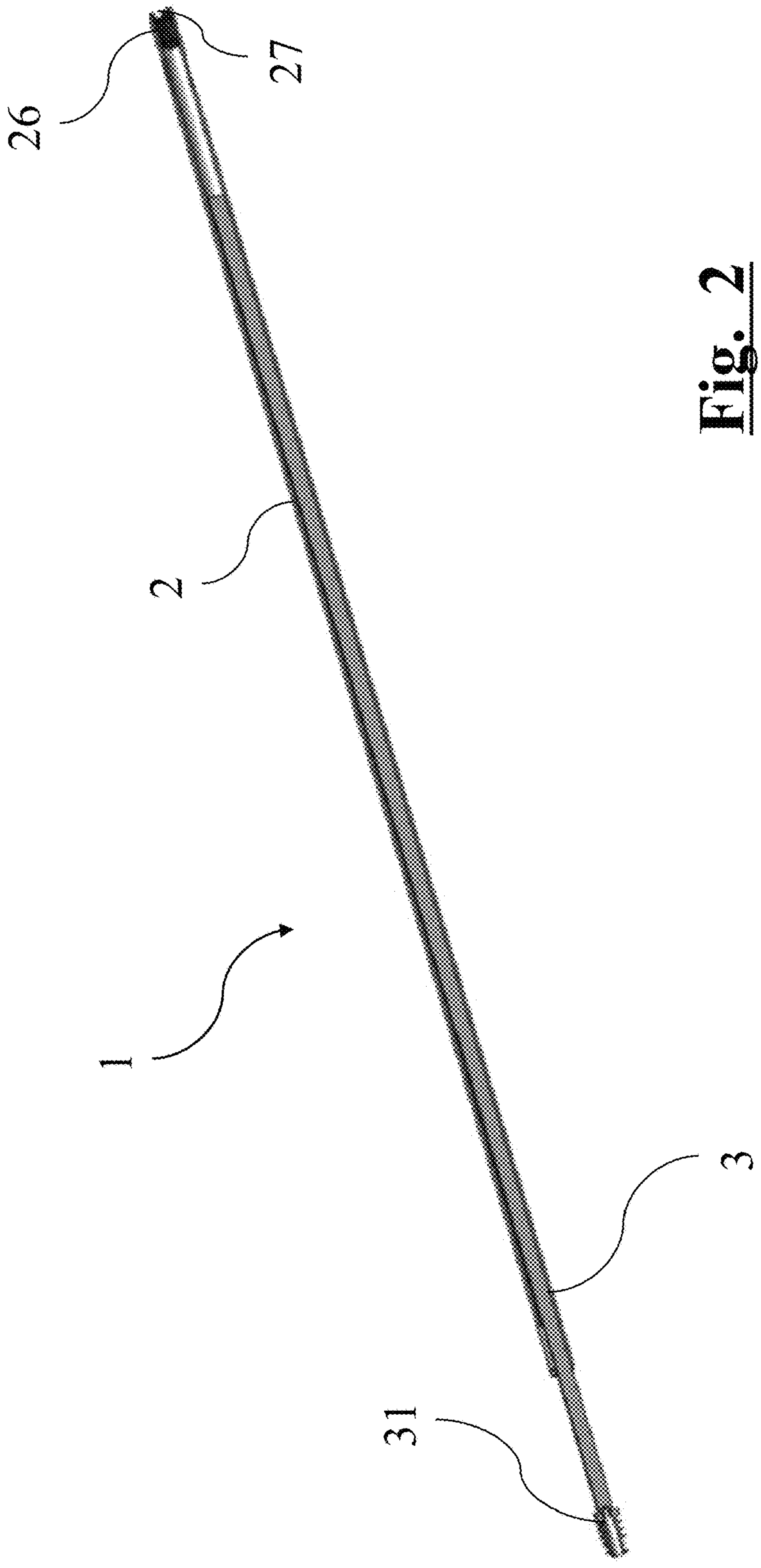
FIG. 2 shows a partial cutaway perspective view of the telescopic intramedullary nail of FIG. 1, with the proximal cap serving as a retainer omitted
Figure 3:
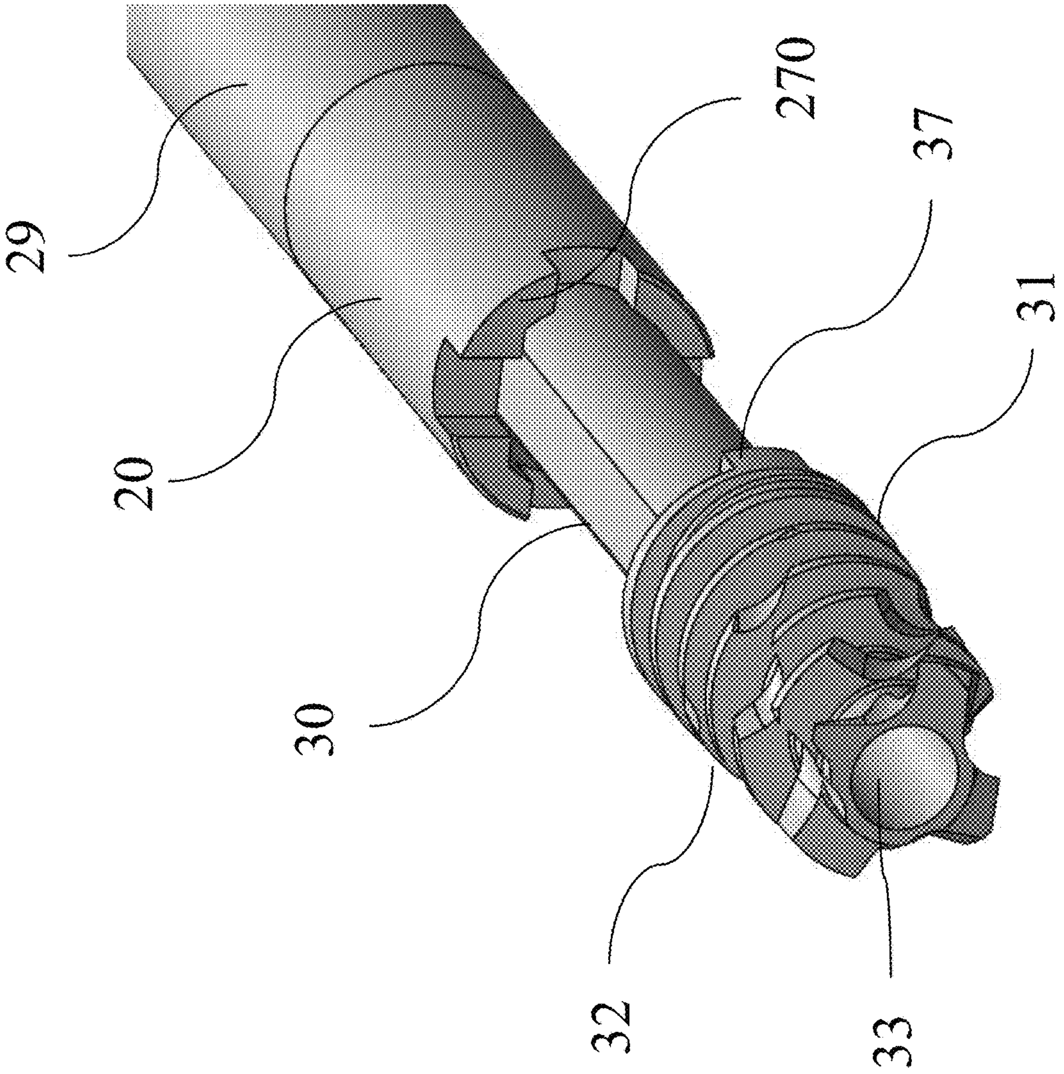
FIG. 3 shows a perspective view of a distal anchoring end of the telescopic intramedullary nail of FIG. 1.
Figure 4:
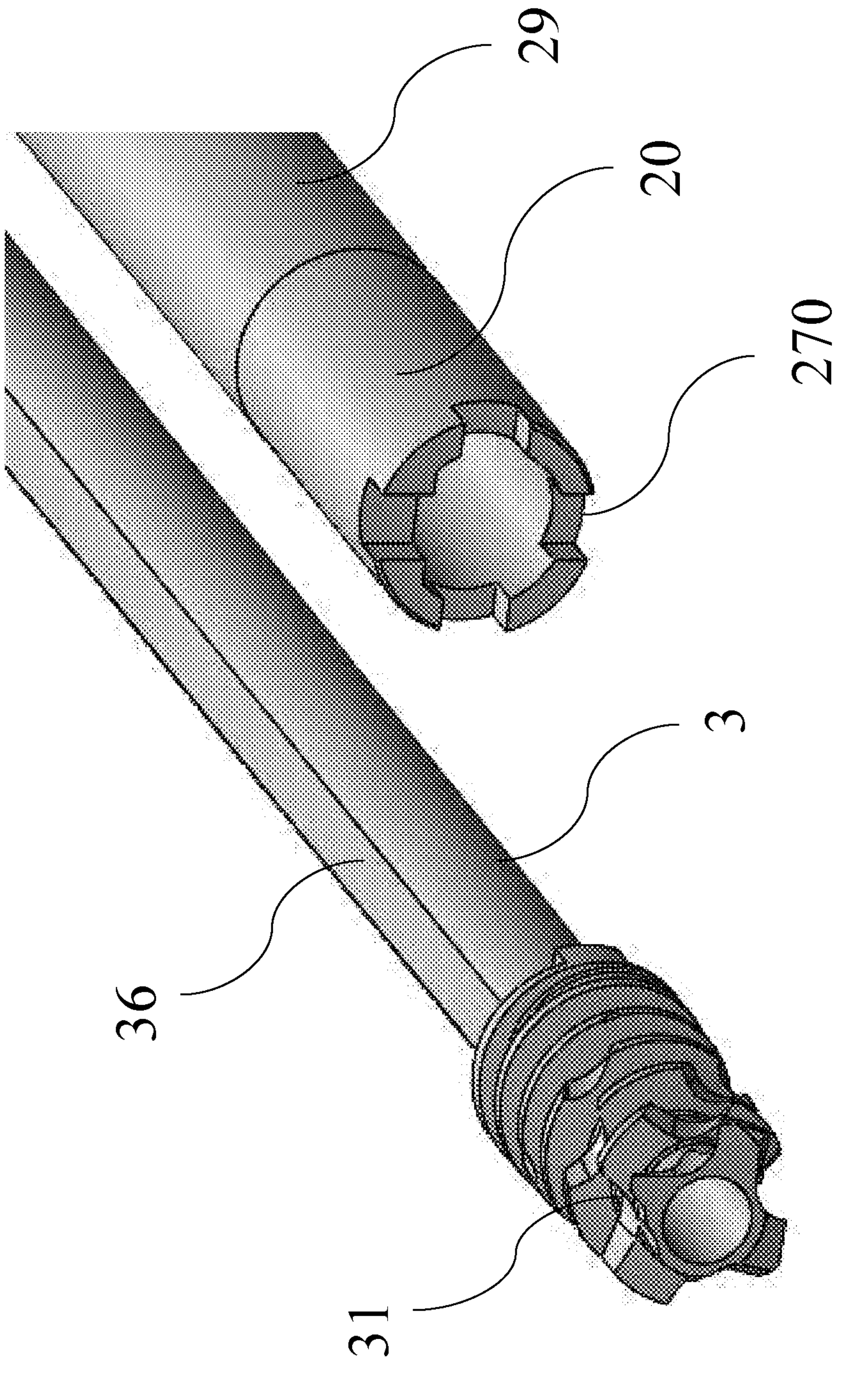
FIG. 4 shows a perspective view of the proximal end illustrated in FIG. 3 with the two components of the rod and of the hollow stem uncoupled.
Figure 5:
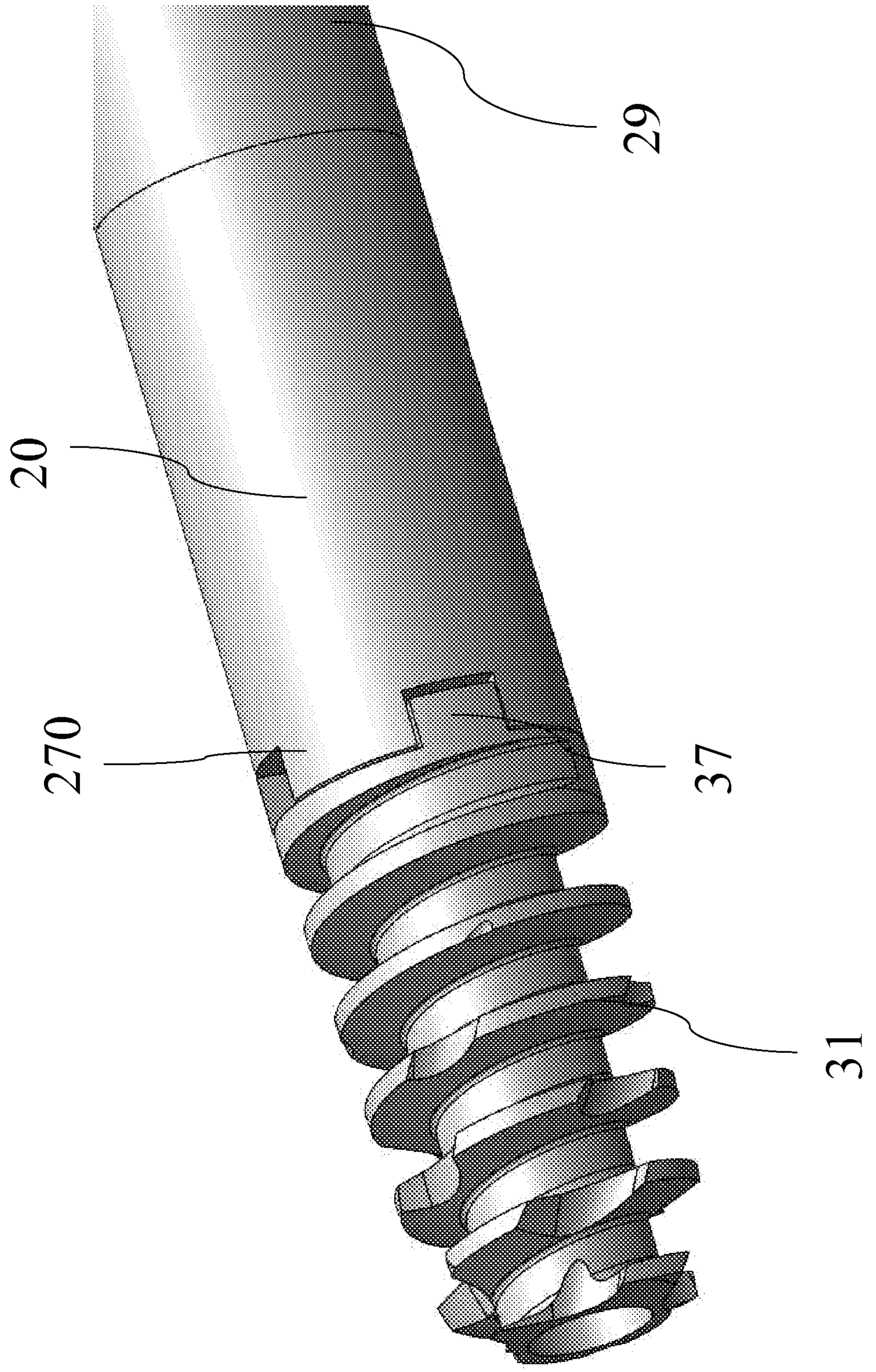
FIG. 5 shows a perspective view of the proximal end illustrated in FIG. 3 in a distal end-of-stroke position of the hollow stem with respect to the rod.
Figure 6:
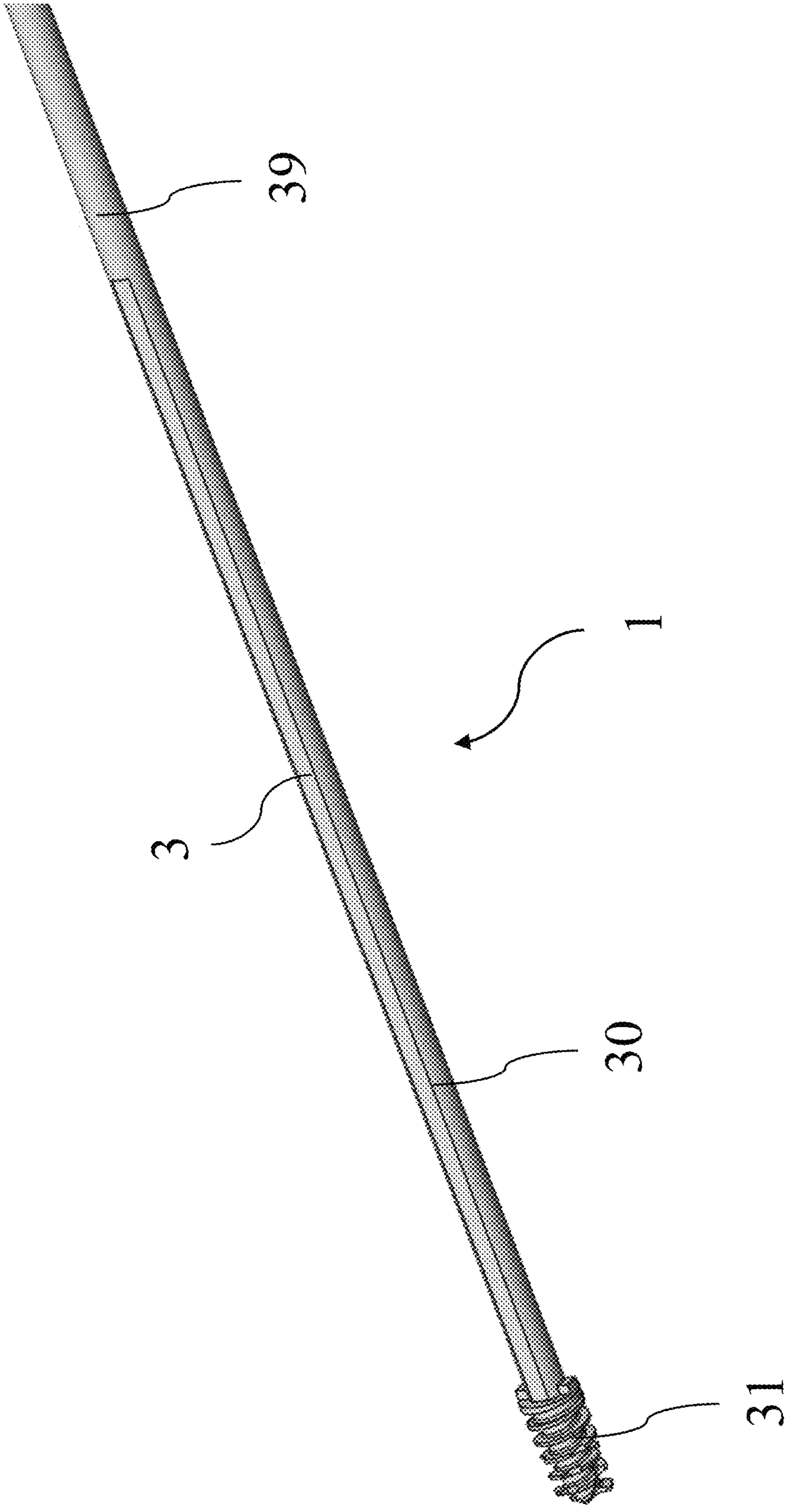
FIG. 6 shows a perspective view of a distal portion of the rod which is part of the telescopic intramedullary nail of FIG. 1.

With reference to the attached figures, an illustrative but non-limiting embodiment of the anterograde telescopic intramedullary nail 1 according to the present invention is described below.

The telescopic intramedullary nail according to the invention is particularly suitable for the treatment of fractures or deformations of long bones 100, such as for example in the case of osteogenesis imperfecta or pseudoarthrosis, in particular in paediatric patients.

The telescopic intramedullary nail 1 generally comprises a hollow stem 2 and a rod 3, the rod 3 being telescopically inserted into said hollow stem 2. Said rod 3 is thus slidingly coupled inside the hollow stem 2.

In the embodiment illustrated in the figure the telescopic coupling provides an external cylindrical surface of the rod 3 which is inserted into an internal cylindrical surface of the hollow stem 2, having a corresponding diameter net of the clearances to allow the telescopic sliding.

However, a shaped section 20 of the hollow stem 2 and a corresponding counter-shaped section 30 of the rod 3 are provided, which have respective internal and external counter-shaped non-circular profiles. These sections, which will be better described below, allow the torque transmission from the hollow stem 2 to the rod 3 during the telescopic intramedullary nail insertion and removal operations.

The mechanical features, and in particular the bending strength, can be sized for the same external diameter so that the strength of the hollow stem 2 and of the rod 3, when not overlapping, are equivalent or the one greater than the other when it is desired to adapt the mechanical strength of the nail to different stresses along the extension of the long bone.

The telescopic intramedullary nail 1 develops along a longitudinal axis X and is delimited by two ends, a distal end of the rod 3 and a proximal end of the hollow stem 2.

It is noted here that the terms terminal and distal refer to a preferred proximal-distal insertion of the telescopic intramedullary nail 1 into the long bone 100 of a patient, preferably a femur, a tibia or a humerus. On the other hand, the possibility that the telescopic intramedullary nail 1 can be implanted following an opposite orientation is not excluded.

The rod 3 of the telescopic intramedullary nail 1 provides, at the distal end, an anchor tip 31 arranged to be internally fixed in the epiphysis of a long bone of the patient.

The anchor tip 31 has a self-threading thread 32, in particular a right-handed thread, arranged to screw into the bone epiphysis, according to modes described below. Said thread 32 ensures a traction stability and an easy penetration into the bone. The fixing of the anchor tip 31 is thus performed with modes which are similar to those of the Fassier-Duval nail, described above with reference to the prior art.

The rod 3 comprises, at the opposite end with respect to the anchor tip 31, the above non-cylindrical shaped section 30 followed by a proximal remaining section 39, which is instead cylindrical. The shaped section 30 is made starting from a section cylindrical by creating a longitudinal flat face 36 which however does not extend up to the remaining section 39.

The hollow stem 2 also consists of the distal shaped section 20, which is welded to an internally cylindrical tube forming a remaining section 29.

The shaped section 20 is thus defined by a sleeve with an internal geometry which is modified with respect to the cylindrical one, and in particular conformed to that of the counter-shaped section 30.

The shaped section 20 further has a front shaping 270, which in the example consists of four equally spaced teeth projecting from the front circumference of the item. The front shaping 270 is arranged to engage with a front counter-shaping 37 obtained on the rod 3, on a shoulder opposite the anchor tip 31. When juxtaposed, the shaping 270 and the counter-shaping 37 allow the transmission of a high torsional torque between the hollow stem 3 and the rod 2.

The remaining section 29 of the hollow stem 2 has, at the proximal end, coupling means 25 for an insertion tool. Said coupling means 25 comprise an internal thread 26, made on the internal cylindrical surface of the hollow stem 2. Moreover, said coupling means 25 comprise a front end crenelation 27, comprising projecting portions interspersed with offsets, made on the insertion mouth of the rod 3. Said end crenelation 27 is defined in particular by four equally spaced offsets, that is opposed two by two, which form therefore two diametrical grooves.

The hollow stem 2 of the telescopic intramedullary nail 1 provides, at the proximal end, a terminal head 21 arranged to externally abut against a proximal end of the long bone, lying therefore at least partially outside said bone.

Said terminal head 21 comprises an external conical thread which screws in place into the hole of the proximal entry made on the long bone. The conical thread can be interrupted by an anti-unscrewing groove, provided to increase the stability of the fixing to the bone. Advantageously, the conical thread has such a high conical development as to ensure a high grip in a reduced bone thickness.

The terminal head 21 further comprises a cylindrical thread 28 arranged to screw into the internal thread 26 of the above coupling means 25.

Obviously, in order to meet contingent and specific requirements, a person skilled in the art will be allowed to bring several modifications and alternatives to the above-described invention, all however falling within the scope of protection of the invention as defined by the following claims.

The invention claimed is:

1. A telescopic intramedullary nail for the treatment of fractures or deformations of long bones extended along a longitudinal axis, comprising:

a hollow stem;

a rod telescopically coupled inside said hollow stem, the rod being axially movable relative to the hollow stem over at least a predetermined travel distance; and means for constraining said hollow stem and said rod in rotation about said longitudinal axis during the insertion or during the removal of said telescopic intramedullary nail;

wherein said means for constraining said hollow stem and said rod in rotation comprise at least one shaped section of said hollow stem and one counter-shaped section of said rod, said shaped section and said counter-shaped section having respective internal and external profiles which are non-circular and shaped in a complementary manner;

wherein the counter-shaped section does not involve the whole extension of the rod, a remaining section of the rod being cylindrical;

wherein said rod comprises, at the distal end thereof, an anchor tip configured to be internally fixed inside the distal epiphysis of the long bone of a patient; and wherein the counter-shaped section is located between the anchor tip and the cylindrical remaining section of the rod.

2. The telescopic intramedullary nail according to claim 1, wherein the shaped section does not involve the whole extension of the hollow stem, a remaining section of the hollow stem having a cylindrical internal surface.

3. The telescopic intramedullary nail according claim 1, wherein said shaped section and said counter-shaped section are placed at the distal end of the hollow stem and of the rod, respectively.

4. The telescopic intramedullary nail according to claim 3, wherein said shaped section of the hollow stem is a sleeve added to the distal end of a remaining section defined by an internally cylindrical tube.

5. The telescopic intramedullary nail according to claim 1, wherein said counter-shaped section comprises one or more flat faces in an otherwise cylindrical geometry.

6. The telescopic intramedullary nail according to claim 1, wherein said means for constraining said hollow stem and said rod in rotation further comprises a front shaping at the distal end of said hollow stem arranged to engage with a front counter-shaping of the rod made on a shoulder facing the hollow stem.

7. The telescopic intramedullary nail according to claim 1, wherein said hollow stem comprises a terminal head arranged to externally abut against a proximal cortical of the long bone of a patient.

8. The telescopic intramedullary nail according to claim 7, wherein said terminal head is removably associated with a proximal end of the hollow stem.

9. The telescopic intramedullary nail according to claim 8, wherein the proximal end of the hollow stem comprises a coupling portion for the selective coupling of said terminal head or of a tool for inserting or removing the telescopic intramedullary nail.

10. The telescopic intramedullary nail according to claim 9, wherein said coupling portion comprises an internal thread.

11. The telescopic intramedullary nail according to claim 10, wherein said coupling portion comprises an end crenelation made frontally with respect to the internal thread.

12. A method of insertion of a telescopic intramedullary nail for the treatment of fractures or deformations of long bones wherein said telescopic intramedullary nail is extended along a longitudinal axis and comprises: a hollow stem; a rod telescopically coupled inside said hollow stem;

the rod being axially movable relative to the hollow stem over at least a predetermined travel distance; an interface which constrains said hollow stem and said rod in rotation about said longitudinal axis during the insertion or during the removal of said telescopic intramedullary nail, the method comprising:

a step of assembling the hollow stem and the rod; and a subsequent step of inserting the hollow stem and the rod already assembled inside the medullary cavity of a long bone of a patient;

wherein said interface which constrains said hollow stem and said rod in rotation about said longitudinal axis comprises at least one shaped section of said hollow stem and one counter-shaped section of said rod, said shaped section and said counter-shaped section having respective internal and external profiles which are non-circular and shaped in a complementary manner;

wherein the counter-shaped section does not involve the whole extension of the rod, a remaining section of the rod being cylindrical;

wherein said rod comprises, at the distal end thereof, an anchor tip configured to be internally fixed inside the distal epiphysis of the long bone of the patient; and wherein the counter-shaped section is located between the anchor tip and the cylindrical remaining section of the rod.

13. A method of insertion of a telescopic intramedullary nail according to claim 12, wherein said rod comprises, at the distal end thereof, an anchor tip, and wherein the step of inserting the hollow stem and the rod comprises a step of rotating the hollow stem in order to constrain the rod into rotation so that the anchor tip is screwed inside the distal epiphysis of the long bone of the patient.

* * * * *